United States Patent [19]

Hohenschutz et al.

[11] 4,134,915

[45] Jan. 16, 1979

[54] CONTINUOUS MANUFACTURE OF FORMAMIDE

[75] Inventors: Heinz Hohenschutz, Mannheim; Max Strohmeyer, Limburgerhof; Manfred Herr, Ludwigshafen; Hans Kiefer, Wachenheim, all of Fed. Rep. of Germany

[73] Assignee: BASF Aktiengesellschaft, Ludwigshafen, Fed. Rep. of Germany

[21] Appl. No.: 793,788

[22] Filed: May 5, 1977

[30] Foreign Application Priority Data

May 22, 1976 [DE] Fed. Rep. of Germany ....... 2623173

[51] Int. Cl.$^2$ ............................................ C07C 102/06
[52] U.S. Cl. ................................................. 260/561 R
[58] Field of Search ............................. 260/561 R, 704

[56] References Cited

U.S. PATENT DOCUMENTS

| 1,567,312 | 12/1925 | Wietzel | 260/561 R |
|---|---|---|---|
| 2,106,579 | 1/1938 | Tanner | 260/561 R |
| 2,751,335 | 6/1956 | Carver et al. | 260/704 X |

*Primary Examiner*—Allen B. Curtis
*Attorney, Agent, or Firm*—Keil, Thompson & Shurtleff

[57] ABSTRACT

Formamide is manufactured continuously from methyl formate and gaseous ammonia. The reaction is carried out in a reactor at from 30 to 90° C, from 5 to 20% by volume of the reactor output is drawn off continuously and fed to the formamide working-up stage, and the remainder of the reactor output is cooled, in an external circuit maintained by means of a pump, to from 25 to 60° C and is mixed with the amount of fresh methyl formate required for steady-state operation, after which the appropriate amount of gaseous ammonia is introduced into the stream of liquid through a jet, by the sucking-jet principle, and the stream of liquid is recycled to the reactor.

5 Claims, No Drawings

CONTINUOUS MANUFACTURE OF FORMAMIDE

The present invention relates to an improved process for the continuous manufacture of formamide by reacting methyl formate with gaseous ammonia.

The manufacture of formamide in accordance with the reaction

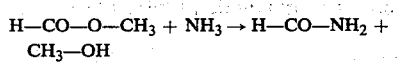

has been disclosed. However simple this equation may appear, the reaction presents great difficulties in industrial operation. The essential reason is that on the one hand the reaction is highly exothermic whilst on the other hand the solubility of gaseous ammonia in the reaction mixture decreases with increasing temperature. It is therefore necessary, as proposed in German Pat. No. 924,928, to carry out the reaction at the relatively low temperature of from 10 to 35° C and this no longer permits simple cooling with industrial water. Accordingly, expensive and energy-intensive cooling units are necessary, and whilst these permit the reaction to be carried out they also slow it down compared to the rate of reaction in the inherently desirable temperature range of from about 50 to 70° C. However, even if the process of German Pat. No. 924,928 were to be modified to operate at a higher temperature, by conventional industrial design methods, other disadvantages would have to be tolerated. The higher temperature would increase the pressure in the reactor to a value of from about 2 to 5 bars (including the hydrostatic pressure). Accordingly, the ammonia, which is available at atmospheric pressure, would have to be compressed, which would virtually annul the principal economic advantage, namely the ability to use ammonia gas at atmospheric pressure.

For these reasons, the industrial synthesis of formamide has hitherto not been carried out with gaseous ammonia but with liquid ammonia (cf. Ullmanns Enzyklopadie der technischen Chemie, third edition, volume 7, page 674); it is true that this process has been fully developed but it is economically unsatisfactory because of the need to liquefy the ammonia.

It is an object of the present invention to improve the economics of the continuous synthesis of formamide from methyl formate, using gaseous ammonia, by a new industrial embodiment of this synthesis.

We have found that this object is achieved by an improved process for the continuous manufacture of formamide from methyl formate and gaseous ammonia, wherein the reaction is carried out in a reactor at from 30 to 90° C, from 5 to 20% by volume of the reactor output is drawn off continuously and fed to the formamide working-up stage, and the remainder of the reactor content is cooled, in an external circuit maintained by means of a pump, to from 25 to 60° C and is mixed with the amount of fresh methyl formate required for steady-state operation, after which the appropriate amount of gaseous ammonia is introduced into the stream of liquid through a jet, by the sucking-jet principle, and the stream of liquid is recycled to the reactor.

The stated range of ratios of recycled reactor output to reactor output withdrawn from the process cycle, namely from 4 : 1 to approx. 20 : 1, corresponds to the range of technically and economically optimal embodiments. Whilst higher ratios are technically possible, they are economically undesirable, and if lower ratios are used, the volume of liquid available is no longer adequate to ensure good distribution of the incoming ammonia in the liquid jet.

On the basis of the recycle ratio, which is preferably from 8 : 1 to 12 : 1, the reactor capacity and the temperature, which may be chosen at random within the stated range (though reactor temperatures of from 50 to 60° C are particularly advantageous economically), the design of the installation, and the energy consumption, can be calculated. If, for example, 4.5 tonnes of formamide are to be produced per hour, at a temperature of 50° C and using a recycle ratio of 10 : 1, about $5 \cdot 10^6$ Joule of heat must be removed per hour via the external cooling system, corresponding to an industrial water consumption of about 110 m³/hour. Because of the relatively high temperature, the pressure at the bottom of the conventional vertical cylindrical reactor of 7 m³ capacity is, including the hydrostatic pressure, about 2.1 bars, i.e. the pump which maintains the cooling circuit must provide a power of about 30 kW, allowing for the pipeline resistance. Furthermore, 6 tonnes of fresh methyl formate must be introduced into the cooling circuit per hour, advantageously after the reaction mixture has been cooled, and 2,200 cubic meters (S.T.P.) ($\approx$ 1.7 tonnes) of ammonia have to be introduced per hour. On the basis of the conventional rules — namely the impulse rule and the Bernoulli equation — it follows that the linear speed of the liquid jet in the sucking-jet nozzle must be from about 20–40 m/sec. This value varies slightly depending on the type of nozzle used. The various types, which all work on the principle of the sucking-jet nozzle, of which the water jet pump is the best-known example, are commercially available or can readily be produced to conform to specific performance values, so that further details are unnecessary. For reasons of corrosion, nozzles made from chromium-nickel steel are preferred.

In order to avoid phase separation, the reactor is preferably kept constantly filled with liquid. Furthermore, it is advisable to introduce the liquid jet, containing ammonia, into the reactor from below, by the shortest path. This method dispenses with mixing and distributing equipment and devices, e.g. stirrers or packings, since the liquid circuit ensures adequate mixing. Preferably, the reactor, pipelines, coolers, pump and valves are, as usual, made from chromium-nickel steel. The above comments apply, except for the use of the sucking-jet nozzle essential to the invention, to the conventional design of installations for liquidphase synthesis under slightly superatmospheric pressure and with external cooling. Of course, depending on individual circumstances, other arrangements can be used equally well, e.g. it is possible to use an air cooler instead of a water cooler or a mixing tube instead of a reactor. However, the maintenance of turbulent flow, necessary when using a mixing tube, requires more energy than carrying out the reaction in a conventional cylindrical reactor. In view of the diverse possible embodiments, the only point to be singled out as being essential to the process is that a sucking-jet nozzle is always used to introduce the gaseous ammonia, since only this permits achieving the advantages of the process according to the invention.

From a chemical point of view, it should be emphasized that using the new process the reaction conforms virtually ideally to the stated equation. Neither catalysts, nor excess ammonia or methyl formate, are required. The fact that the reaction takes place stoichiometrically represents a further essential advantage compared with the excess (up to 1.54-fold) of ammonia required, because of inadequate solubility, in the method described in German Pat. No. 924,928.

The reaction mixture is worked up in the conventional manner to give formamide, which is obtained in yields of about 99%.

The essential advantages of the process according to the invention are that ammonia can be used under atmospheric pressure and accordingly does not require a separate compression process, and that the ammonia immediately disperses so finely in the liquid jet that phase separation of the liquid-gas mixture no longer occurs even at the high reaction temperatures used according to the invention. As a result of it now being possible to use higher temperatures, the space-time yields are increased compared to those achieved with the method using the conventional temperatures of about 30° C. The advantage resulting from being able to use stoichiometric amounts of the starting materials has already been pointed out in another context.

Compared to the synthesis using liquid ammonia, the continuing operating costs (ignoring the investment required, which is also lower) are reduced by about 20–30 percent.

EXAMPLE

In the steady-state continuous operation of a vertical cylindrical chromium-nickel steel reactor of 7.5 m internal height and 1.1 m internal diameter, 90 m$^3$ of reaction mixture left the reactor per hour, and 8 m$^3$ thereof were worked up. The remainder was first fed, via an external circuit maintained by means of a pump (30 kW power), to a cooler operated with industrial water, in which the mixture was cooled from the reactor temperature of 55° C to 35° C. The reaction mixture was then mixed, first with 6.4 m$^3$ (= 6.2 tonnes) of 97% strength methyl formate, and then, using a sucking-jet nozzle, with 2,150 m$^3$ (S.T.P.) (= 1.7 tonnes) of gaseous ammonia available under atmospheric pressure; immediately thereafter, the resulting mixture was returned to the reactor, from below, against a pressure of about 2.7 bars.

Working-up in the conventional manner gave, per hour, 4.5 tonnes of formamide of 99% purity.

We claim:

1. In a process for the continuous manufacture of formamide from methyl formate and gaseous ammonia, the improvement which comprises carrying out the reaction in a reactor at from 30 to 90° C, drawing off from 5 to 20% by volume of the reactor output continuously and feeding it to a formamide working-up stage, and cooling the remainder of the reactor output to from 25 to 60° C in an external circuit maintained by means of a pump and mixing it with the amount of fresh methyl formate required for steady-state operation, after which the amount of gaseous ammonia required for steady-state operation is introduced into the resulting stream of liquid through a jet, by the sucking-jet principle, and the stream of liquid is recycled to the reactor.

2. A process as claimed in claim 1, wherein the volume ratio of reactor output recycled to reactor output fed to the formamide working-up stage is 8 : 1 to 12 : 1.

3. A process as claimed in claim 1, wherein the reaction is carried out at 50 to 60° C.

4. A process as claimed in claim 1 wherein the linear speed of the liquid flowing through said sucking-jet nozzle is from about 20 to 40 m/sec.

5. A process as claimed in claim 4 wherein the reaction is carried out at 50° to 60° C, and the volume ratio of reactor output recycled to reactor output fed to the formamide working-up stage is 8:1 to 12:1.

* * * * *